United States Patent [19]

Schuberth et al.

[11] 4,301,023
[45] Nov. 17, 1981

[54] CHOLESTERIC COMPOSITIONS

[75] Inventors: Winfried Schuberth, West Carrollton, Ohio; John F. Hanny, Racine, Wis.

[73] Assignee: American Thermometer Co., Inc., Dayton, Ohio

[21] Appl. No.: 161,789

[22] Filed: Jun. 23, 1980

[51] Int. Cl.$^3$ .............................................. C09K 3/34
[52] U.S. Cl. .................................. 252/299.7; 424/59; 424/63
[58] Field of Search ................. 252/299, 408; 73/356, 73/432; 106/316; 424/7, 59, 63

[56] References Cited

U.S. PATENT DOCUMENTS

| | | | |
|---|---|---|---|
| 3,441,513 | 4/1969 | Woodmansee | 252/299 |
| 3,529,156 | 9/1970 | Fergason et al. | 252/299 |
| 3,533,399 | 10/1970 | Goldberg et al. | 252/299 |
| 3,576,761 | 4/1971 | Davis | 252/299 |
| 3,600,060 | 8/1971 | Churchill | 252/299 |
| 3,771,065 | 11/1973 | Goldberg et al. | 252/299 |
| 3,885,982 | 5/1975 | Fergason | 252/299 |
| 3,920,574 | 11/1975 | Brown, Jr. et al. | 252/299 |
| 3,969,264 | 7/1976 | Davis | 252/299 |
| 3,974,317 | 8/1976 | Sharpless | 252/299 |
| 4,045,383 | 8/1977 | Koff | 252/299 |

*Primary Examiner*—Teddy S. Gron
*Attorney, Agent, or Firm*—Mason, Kolehmainen, Rathburn & Wyss

[57] ABSTRACT

A combination of two or more shear-sensitive cholesteric compounds in a carrier (which can be a third cholesteric ester) creates a mixture of liquid crystals which may be colored or clear which when subjected to a rubbing action produce various colored crystal formulations due to the shearing of the crystals in the physical application of the formulation to a surface. A variety of colors from light red to dark blue can be created which disappear as the cholesteric esters are absorbed into the surface. During the application of these formulations a desirable color display is created which adds to the attractiveness of the system, particularly as cosmetic ingredients. Because the cholesteric materials are usually esters of cholesterol, they are readily taken up by the skin and are desirable components for cosmetic formulations.

1 Claim, No Drawings

CHOLESTERIC COMPOSITIONS

This invention relates to compositions of liquid crystal compounds in the form of 100% liquid crystal solids or as aqueous suspensions of liquid crystal solids. These compositions produce a multitude of colors when sheared by mechanical action on an opaque surface. Most particularly this invention relates to formulations of shear-sensitive cholesteryl esters in a 100% solids form or in a carrier in the form of aqueous oleaginous gels which when stimulated my mechanical shearing action undergo a variety of color changes which contribute to the aesthetic appeal of the formulations. These unique formulations possess the inherent capability to display a single color over a wide temperature range (0° C.–50° C.) until mechanically sheared, thereby producing a rainbow display of iridescent colors. This initial color is selectively attained by altering the composition of the three liquid crystal compounds. When such compositions are applied to the skin the cholesteryl esters impart moisturizing and softening action to the skin and serve as a replacement of natural oils because cholesterol is a naturally occurring compound which is well tolerated by the skin, as are its esters.

BACKGROUND OF THE INVENTION

Liquid crystals are a well-known phenomenon. The first observation of the phenomenon was made in 1888 on cholesteryl benzoate, which melts at 145° C. but to a cloudy liquid which does not become clear until 179° C. Although apparently a liquid, the cloudy melt showed optical properties of a crystal and so the term "liquid crystal" was adopted.

There are three main groups of liquid crystals: smectic, nematic and cholesteric. Cholesteric liquid crystals have been used to map temperature patterns, as well as infra-red, microwave and ultrasonic fields through converting these energy forms into heat.

Until the discovery of liquid crystals, all matter had been commonly classified in three states: solid, liquid or gas, with increasing molecular disorder occurring as one passes from the solid to the gaseous state. The liquid crystalline state is in many respects a fourth state of matter intermediate in molecular ordering between a crystalline solid and an ordinary liquid. Hence it is more accurately named as the "mesomorphic" or intermediate state. However, the term "liquid crystal," first used by Lehmann in 1889, has remained in use because it describes so directly the properties of this intermediate state—the mechanical properties of liquids combined with the optical properties of crystals.

Between all molecules attractive and repulsive forces interact. In a crystalline solid the attractive forces between the molecules are strong enough to hold them packed into a regular three-dimensional geometrical array over large volumes. Hence crystals are said to show long range ordering of the molecules. One result of this ordering is that for certain crystals the physical properties, for example, the speed at which light travels through the crystal, will vary with the angle between the direction in which they are measuring and the axes of the crystal (which are defined by the way the molecules pack together). This variation of properties with direction of measurement is called anisotropic behavior.

In an ordinary liquid the cohesion between the molecules has been reduced to a point where they are free to move and so they can adopt a radom arrangement. There is still some degree of ordering as each molecule can be considered as being surrounded by a spherical shell of its neighbors. However, this spherical arrangement only holds for the short distances between neighboring molecules. Over longer distances the "short range" ordering of the molecules breaks down to form a random arrangement. Because of this long-range randomness the physical properties of a liquid are the same in whichever direction they are measured; that is, the liquid behaves isotropically.

For most organic compounds the transition from the crystalline state to the isotropic liquid occurs rapidly once the cohesive forces holding the molecules in a fixed arrangement in the crystal have been overcome. There is no stable intermediate level of molecular cohesion between the high level present in the crystal and the lower level present in the isotropic liquid. But some organic compounds, because of their rod-like crystalline shape and the particular attractive forces between the molecules, can have a stable intermediate level of molecular cohesion. It is these compounds which form "liquid crystals." In the liquid crystalline state the cohesion between the molecules has been reduced enough, compared to the crystalline solid, to allow a rearrangement of the molecules. Some freedom of movement is possible (thus the liquid properties) but not enough to allow completely random alignment of the rod-like molecules (thus the anistropic crystalline behavior). Eventually, with a further increase of, for example, temperature, the cohesive forces in the liquid crystalline state (mesophase) are overcome and an ordinary isotropic liquid is formed.

The three main subdivisions or mesophases of the liquid crystalline state (smectic, nematic and cholesteric), all have some basic properties in common, such as birefringence, but they differ in their molecular structure and other properties.

(a) Smectic mesophase: in the smectic mesophase, the molecules are arranged in "raft like" layers, with their axes parallel, either normal (that is, at right angles) to the plane of the layer, or tilted. The molecular packing within the layer can be either regular or random.

(b) Nematic mesophase: in the nematic phase the long axes of the molecules retain a parallel alignment but, in contrast to the smectic phase, there is no separation into layers so that otherwise their positional arrangement is random. Thus this type of liquid crystal is that much closer to an ordinary isotropic liquid than the smectic phase.

(c) Cholesteric mesophase: strictly speaking, the cholesteric phase is a "twisted" form of the nematic phase. There is no layering and the positional arrangement of the molecules is random, but the direction in which the parallel molecules are aligned twists round as one passes through the cholesteric phase. This twisting forms a screw-like, helical arrangement of the molecules in the cholesteric phase, like the steps of a spiral staircase. Because of this helical structure a property very important to the optical behavior of the cholesteric phase is produced; that is, a periodicity corresponding to the pitch of the helix (the distance between areas where the molecules are pointing in the same direction) which is roughly equal to the wavelength of visible light.

The most impressive and striking optical property of the cholesteric liquid crystal is that under the right conditions it displays a vivid color when illuminated with white light. Basically, the cholesteric liquid crystal is behaving like a mirror reflecting light falling onto it, but it is no ordinary mirror since it picks out and reflects only light of a certain wavelength, a certain color, which corresponds to the pitch of the helix. By regarding the molecular arrangement as a set of thin birefringent plates (the molecular layers of roughly parallel alignment) stacked in a helix one is able to analyse the rather unusual optical properties of the phase. Birefringence is the property whereby light passing through a crystal experiences double refraction because it can have two different velocities as a result of the anisotropy of the crystal. Light rays entering the stack pass from plate to plate undergo a small sideways bending at each transition because of the birefringent refractive properties of each plate. This sideways twisting of the light rays causes the light to become circularly polarised as it travels further down through more plates so that it ends up spiralling along the axis of the helix. A further result of the birefringence of the plates is that the light separates into a fast and a slow wave between which a phase shift will occur (light waves from the fast component will get out of step with light waves from the slow component). At certain points along the helix the phase shift between the two wave sets up a standing wave reflecting circularly polarised light back out of the cholesteric liquid crystal. The standing wave will have a wavelength equal to the pitch of the helix and it is this color which is seen. For light of other wavelengths the conditions for setting up a standing wave are not present and so this light will continue on through the cholesteric liquid crystal unreflected. Thus if white light falls on the crystal one color will come back out as a reflected wavelength while other colors will be transmitted onwards. If the light that is transmitted is finally absorbed into a dark background only the reflected wavelength is seen, as a pure iridescent color.

Described above is a characteristic method of using a cholesteric liquid crystal, that is, as a thin film of material deposited on a light-absorbing black background. Subjected to the appropriate temperature or other stimuli the film reflects the vivid colors of the rainbow. For example, a sheet of cholesteric liquid crystal sensitive in the appropriate temperature range (25° C. to 31° C.) will change color rapidly in response to body warmth if it is handled. The color observed depends on the pitch distance of the helix in the crystal and this pitch can be easily altered. The distance between the molecular layers in the crystal which determines the final pitch distance depends on a balance of weak intermolecular attractions and repulsions. In response to a change in this balance by a stimulus, such as a temperature change, shear force and presence of other chemicals, a color change will be seen. It is this direct, visible response to stimuli which gives cholesteric liquid crystals their important versatility as detector systems. The stimuli can either interact directly with the balance of molecular forces in the crystals or can be converted into a stimulus which does interact.

SUMMARY OF THE INVENTION

We have found that combinations of two or more esters of cholesterol suspended in an oleaginous carrier or in an aqueous emulsion provide liquid compositions which are desirable for application to opaque surfaces such as skin. A combination of two cholesteryl esters dissolved in a third cholesteryl ester such as a fatty acid ester of cholesterol forms suitable suspensions for application to the body. Similar combinations of cholesteryl esters in aqueous suspension with appropriate emulsifying agents form lotions which can be likewise applied to the body. At ambient temperature these various formulations containing liquid crystals are subjected to shearing during the normal rubbing process which occurs during the application of a cream, gel, or aqueous suspension to a surface, thus causing the cholesteryl esters, which are shear-sensitive liquid cyrstals, to produce a variety of colors during application. These colors remain until the cholesteryl esters are absorbed by the skin and create a desirable artistic display which enhances the impression caused by the formulation.

The liquid crystals which are used in this invention are cholesteric liquid crystals which have the helical structure described above. An organic solvent cannot be used with such crystals because when the crystals are dissolved they lose their distinctive characteristics and no longer exhibit the iridescent colors. Therefore if two or more cholesteric liquid crystals are to be combined in a liquid formulation, this is generally done by dissolving the liquid crystals in a third cholesteric material.

In this invention the cholesteric liquid crystals are usually fatty acid esters of cholesterol, such as the following:

| Cholesteryl Ester | Mesomorphic Range |
|---|---|
| Cholesteryl acetate | 94–114° C. |
| Cholesteryl benzoate | 149–178° C. |
| Cholesteryl butyrate | 99–111° C. |
| Cholesteryl caprinate | 82–90° C. |
| Cholesteryl caprylate | 92–106° C. |
| Cholesteryl 4-carbomethoxyoxybenzoate | 127–274° C. |
| Cholesteryl chloride | 62–96° C. |
| Cholesteryl cinnamate | 158–210° C. |
| Cholesteryl 4-cyano cinnamate | 163–274° C. |
| Cholesteryl decanoate | 83–90° C. |
| Cholesteryl 3,4-diethoxybenzoate | 128–146° C. |
| Cholesteryl heptanoate | 93–112° C. |
| Cholesteryl hexanoate | 98–100° C. |
| Cholesteryl laurate | 88–92° C. |
| Cholesteryl myristate | 71–84° C. |
| Cholesteryl octanoate | 94–108° C. |
| Cholesteryl oleate | 45–46° C. |
| Cholesteryl pelargonate | 78–91° C. |
| Cholesteryl pentanoate | 93–99° C. |
| Cholesteryl 3-phenyl-propionate | 108–112° C. |
| Cholesteryl propionate | 96–113° C. |
| Cholesteryl undecylate | 89–92° C. |
| Cholesteryl valerate | 91–97° C. |
| Cholesteryl ceratrate ($C_{36}H_{54}O_4$) | 139–174° C. |

Preferred esters are cholesteryl pelargonate, benzoate, cinnamate, adipate, p-nitrobenzoate, 3,4-dinitrobenzoate, 2-ethylhexanoate, and cholesteryl chloride. A preferred combination contains two or more cholesteryl esters of the foregoing type with a cholesteryl ester which exhibits limited color, such as one of the cholesteryl carbonates including cholesteryl cetyl carbonate, cholesteryl ethyl carbonate, cholesteryl methyl carbonate, cholesteryl oleyl carbonate, cholesteryl isostearyl carbonate, cholesteryl 2-(ethoxyethoxy)ethyl carbonate, cholesteryl 2-methoxyethyl carbonate, cholesteryl propargyl carbonate and cholesteryl methallyl carbonate.

The combination of two cholesteric liquid crystal materials results in a formulation which exhibits colors over a wide temperature range, that is, from about 0° to about 50° C. Ordinarily one cholesteric liquid crystal material will exhibit colors over a relatively narrow temperature range of about 1° to 3° C. Thus individual cholesteric liquid crystals have a narrow range of applicability, whereas a combination of specifically selected cholesteric liquid crystals can give the wide color range which is desired. By varying the relative amounts of the cholesteric liquid crystal materials in the composition, different hues can be obtained, another desirable feature of this invention.

DESCRIPTION OF THE PREFERRED EMBODIMENTS

The preferred embodiments are combinations of cholesteryl chloride and cholesteryl nonanoate with cholesteryl isostearyl carbonate and dispersed in water with a suitable dispersing agent such as a water-soluble carboxy-vinyl resin such as carboxypolymethylene (marketed under the trademark Carbopol by B. F. Goodrich Company). The combination of cholesteryl nonanoate, cholesteryl chloride and cholesteryl isostearyl carbonate carbonate can comprise from 5% to 50% of the weight of the emulsion, as a practical range. In many applications the combination of these three cholesteric liquid crystal materials comprises 100% of the formulation. The preferred formulation contains from 20% to 35% cholesteryl chloride, 20% to 35% cholesteryl nonanoate and the remainder cholesteryl isostearyl carbonate (30% to 60%).

Other dispersing agents can be used in these liquid crystal compositions, such as xanthan gum (a polysaccharide sold under the name KELTROL-F) of molecular weight of about 1,000,000 which is a cream-colored free-flowing powder which dissolves readily in water; diethylaminoethylcellulose; carboxymethylcellullose; hydroxyethylcellulose (sold under the trademark CELLOSIZE by Union Carbide Corporation); and poly-(ethylene oxide) homopolymers of molecular weight greater than 100,000 (sold by Union Carbine Corporation under the POLYOX trademark).

Suitable combinations of cholesteryl nonanoate, cholesteryl chloride and cholesteryl isostearyl carbonate and the properties thereof are set forth in the following table. These formulas exhibit a single iridescent color over a range of 0° C. to 50° C. when maintained in a stable state. When a mechanical shearing force (rubbing) is induced, a rainbow of iridescent colors is displayed. The following table describes variations in composition to yield specific stable-state colors.

| Cholesteryl Nonanoate | Cholesteryl Chloride | Cholesteryl Isostearyl Carbonate | Formulation Color at 26° C. (Prior To Shearing) |
| --- | --- | --- | --- |
| 33.8% | 33.8% | 32.4% | water clear |
| 33.1% | 33.1% | 33.8% | water clear |
| 32.5% | 32.5% | 35.0% | water clear |
| 31.8% | 31.8% | 36.4% | light red |
| 31.2% | 31.2% | 37.6% | light red |
| 30.8% | 30.8% | 38.4% | light red |
| 30.1% | 30.1% | 39.8% | red |
| 29.6% | 29.6% | 40.8% | red |
| 29.1% | 29.1% | 41.8% | red |
| 28.6% | 28.6% | 42.8% | orange |
| 28.1% | 28.1% | 43.8% | orange |
| 27.6% | 27.6% | 44.8% | yellow-orange |
| 27.2% | 27.2% | 45.6% | yellow-orange |
| 26.7% | 26.7% | 46.6% | yellow |
| 26.3% | 26.3% | 47.4% | yellow-green |
| 25.9% | 25.9% | 48.2% | green |
| 25.5% | 25.5% | 49.0% | green |

The invention is disclosed in further detail by means of the following examples which are presented only for purposes of illustration.

EXAMPLE 1

One hundred grams of a mixture of cholesteric liquid crystals containing 29.6% by weight cholesteryl nonanoate, 29.6% cholesteryl chloride and 40.8% cholesteryl isostearyl carbonate was warmed to 70° C., forming an oily liquid. This liquid was added slowly to 300 grams of hot (70°) water with mild agitation. After the liquid crystals were added 75 grams of carboxypolymethylene (Carbopol 940) was added with agitation. When all the Carbopol was in solution (3 to 5 minutes) approximately two milliliters of 10% sodium hydroxyde solution was added and the composition gelled immediately.

The resultant gel was clear with droplets of red liquid crystals uniformly suspended throughout the gel, but when applied to the skin and rubbed therein it formed a variety of iridescent colors from red to purple until the cholesteryl esters were absorbed into the skin. It was isotropic above 50° C.

EXAMPLE 2

One hundred grams of a mixture of cholesteric liquid crystals containing 25.5% cholesteryl nonanoate, 25.5% cholesteryl chloride and 49.0% cholesteryl isostearyl carbonate was treated as in Example 1. The resultant gel was clear with droplets of green liquid crystals uniformly suspended throughout the gel.

We claim:

1. A single-color composition of shear-sensitive liquid crystal compounds consisting essentially of:
   25–34% cholesteryl nonanoate,
   25–34% cholesteryl chloride and
   32–50% cholesteryl isostearyl carbonate
suspended in an oleaginous carrier or an aqueous emulsion, said composition producing a variety of colors when subjected to shearing on the surface of an inert substrate, while maintaining the same color over a wide temperature range.

* * * * *